(12) United States Patent
Sreekumari et al.

(10) Patent No.: US 12,354,257 B2
(45) Date of Patent: Jul. 8, 2025

(54) METHOD AND SYSTEM FOR AUTOMATIC SEGMENTATION AND PHASE PREDICTION IN ULTRASOUND IMAGES DEPICTING ANATOMICAL STRUCTURES THAT CHANGE OVER A PATIENT MENSTRUAL CYCLE

(71) Applicant: GE Precision Healthcare LLC, Wauwatosa, WI (US)

(72) Inventors: Arathi Sreekumari, Calicut (IN); Pavan Annangi, Bangalore (IN); Bhushan Patil, Pune (IN); Stephan Anzengruber, Ried im Innkreis (AT)

(73) Assignee: GE Precision Healthcare LLC, Waukesha, WI (US)

( * ) Notice: Subject to any disclaimer, the term of this patent is extended or adjusted under 35 U.S.C. 154(b) by 524 days.

(21) Appl. No.: 17/728,003

(22) Filed: Apr. 25, 2022

(65) Prior Publication Data
US 2023/0342917 A1 Oct. 26, 2023

(51) Int. Cl.
*G06T 7/00* (2017.01)
*A61B 8/00* (2006.01)
*A61B 8/08* (2006.01)
*G06T 7/11* (2017.01)
*G06T 7/62* (2017.01)

(52) U.S. Cl.
CPC ............ *G06T 7/0012* (2013.01); *A61B 8/085* (2013.01); *A61B 8/463* (2013.01); *A61B 8/466* (2013.01);
(Continued)

(58) Field of Classification Search
CPC ................. G06T 7/0012; G06T 11/206; G06T 2207/20084; G06T 7/11; G06T 7/90;
(Continued)

(56) References Cited

U.S. PATENT DOCUMENTS

2021/0393240 A1\* 12/2021 Han ........................ G06T 7/74
2022/0287622 A1\* 9/2022 Thigpen ............... A61B 5/0816

OTHER PUBLICATIONS

Qi, Charles R., et al., "PointNet: Deep Learning on Point Sets for 3D Classification and Segmentation," Stanford University, Apr. 10, 2017, 19 pages.
(Continued)

*Primary Examiner* — Ajibola A Akinyemi
(74) *Attorney, Agent, or Firm* — McAndrews, Held & Malloy, Ltd.; Daniel Bissing

(57) ABSTRACT

Systems and methods for automatically segmenting and detecting a menstrual cycle phase in ultrasound images of anatomical structures that change over a patient menstrual cycle are provided. The method includes acquiring, by an ultrasound probe of an ultrasound system, an ultrasound image of a region of interest having an anatomical structure that changes over a patient menstrual cycle. The method includes automatically segmenting, by at least one processor of the ultrasound system, an anatomical structure depicted in the ultrasound image. The method includes automatically predicting, by the at least one processor, a menstrual cycle phase based on the segmentation of the anatomical structure. The method includes causing, by the at least one processor, a display system to present at least one rendering of the segmented anatomical structure and the predicted menstrual cycle phase.

20 Claims, 2 Drawing Sheets

(52) U.S. Cl.
CPC ............ *A61B 8/483* (2013.01); *A61B 8/5215* (2013.01); *G06T 7/11* (2017.01); *G06T 7/62* (2017.01); *G06T 2207/10132* (2013.01); *G06T 2207/20081* (2013.01); *G06T 2207/20084* (2013.01)

(58) Field of Classification Search
CPC . G06T 2207/20081; G06T 2207/20132; G06T 2210/41; G06T 11/60; G06T 2207/10132; G06T 2207/30016; G06T 2207/30024; G06T 2207/10016; G06T 2200/24
USPC ......................................................... 382/128
See application file for complete search history.

(56) References Cited

OTHER PUBLICATIONS

Singhal, Nitin, et al., "Automated Assessment of Endometrium from Transvaginal Ultrasound Using Deep Learned Snake," IEEE Xplore, Feb. 16, 2022, pp. 283-286.

Tian, Sukun, et al., "Automatic Classification and Segmentation of Teeth on 3D Dental Model Using Hierarchical Deep Learning Networks," IEEE Access, vol. 7, 2019, Mar. 2019, pp. 84817-84828.

Hu, Szu-Yeu, et al., "Deep Learning-Based Automatic Endometrium Segmentation and Thickness Measurement for 2D Transvaginal Ultrasound," IEEE Xplore, Feb. 16, 2022, pp. 993-997.

Diaz-Pernas, Francisco Javier, et al., "A Deep Learning Approach for Brain Tumor Classification and Segmentation Using a Multiscale Convolutional Neural Network," Healthcare 2021, 9, 153, https://www.doi.org/10.3390/healthcare9020153, pp. 1-14.

Park, Hyenok, "Endometrium segmentation on transvaginal ultrasound image using key-point discriminator," American Association of Physicists in Medicine, vol. 46 (9), Sep. 2019, pp. 3974-3984.

Amyar, A., et al., "Multi-Task Deep Learning Based CT Imaging Analysis for COVID-19: Classification and Segmentation," Computers in Biology and Medicine, vol. 126, Apr. 16, 2020, 7 pages.

Mohamed, Eslam, et al., "Real-time Semantic and Class-agnostic Instance Segmentation in Autonomous Driving," https://www.researchgate.net/publication/346931683, Dec. 2020, 6 pages.

* cited by examiner

METHOD AND SYSTEM FOR AUTOMATIC SEGMENTATION AND PHASE PREDICTION IN ULTRASOUND IMAGES DEPICTING ANATOMICAL STRUCTURES THAT CHANGE OVER A PATIENT MENSTRUAL CYCLE

FIELD

Certain embodiments relate to ultrasound imaging. More specifically, certain embodiments relate to a method and system for automatically segmenting and detecting a menstrual cycle phase in ultrasound images of anatomical structures that change over a patient menstrual cycle.

BACKGROUND

Ultrasound imaging is a medical imaging technique for imaging organs and soft tissues in a human body. Ultrasound imaging uses real time, non-invasive high frequency sound waves to produce a series of two-dimensional (2D) and/or three-dimensional (3D) images.

Ultrasound imaging may involve the segmentation of anatomical structures in ultrasound images for analysis and diagnosis. However, the shape, appearance, size, and/or echogenicity of certain anatomical structures may vary over a time period, such as a patient menstrual cycle. For example, the shape and appearance of an endometrium in an ultrasound image may have a triple line appearance of the endometrial lining during a proliferative phase of a patient menstrual cycle. The endometrium may appear thick and hyperechogenic during a secretory phase of a patient menstrual cycle. The endometrium may appear thin and hyperechogenic during a menstrual phase of a patient menstrual cycle. The endometrium appearance may also change for different pathologies, including endometriosis, endometrial cancer, endometrial polyps, fibroids, endometrial morphology, and the like. Consequently, automatic segmentation of an endometrial cavity from gynecological uterine ultrasound scans, or other anatomical structures that change over a time period, may be difficult due to the high variability in the shape, appearance, size, and/or echogenicity of the anatomical structure.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY

A system and/or method is provided for automatically segmenting and detecting a menstrual cycle phase in ultrasound images of anatomical structures that change over a patient menstrual cycle, substantially as shown in and/or described in connection with at least one of the figures, as set forth more completely in the claims.

These and other advantages, aspects and novel features of the present disclosure, as well as details of an illustrated embodiment thereof, will be more fully understood from the following description and drawings.

DETAILED DESCRIPTION

Figure 1:
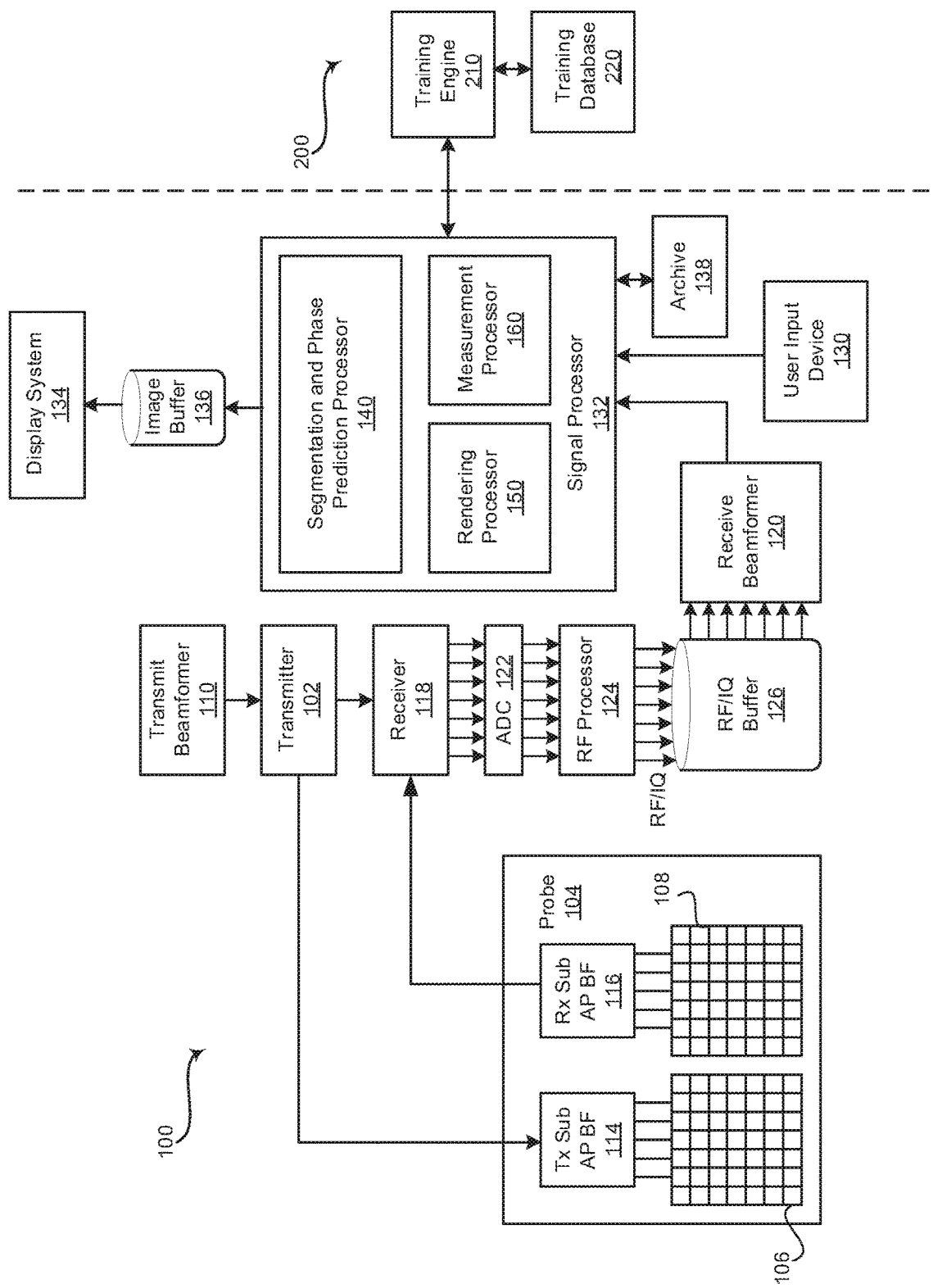
FIG. 1 is a block diagram of an exemplary ultrasound system that is operable to automatically segment and detect a menstrual cycle phase in ultrasound images of anatomical structures that change over a patient menstrual cycle, in accordance with various embodiments.

Certain embodiments may be found in a method and system for automatically segmenting and detecting a menstrual cycle phase in ultrasound images of anatomical structures that change over a patient menstrual cycle. Aspects of the present disclosure have the technical effect of automatically segmenting anatomical structures having a high variability in shape, appearance, size, and/or echogenicity over a time period. Various embodiments have the technical effect of predicting a menstrual cycle phase in ultrasound images of anatomical structures that change over a patient menstrual cycle. Certain embodiments have the technical effect of providing a single network architecture configured to segment the anatomical structure and predict the phase of the time period. Aspects of the present disclosure have the technical effect of generating renderings of the segmented anatomical structure for display with the predicted phase of the time period.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general-purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized, and that structural, logical and electrical changes may be made without departing from the scope of the various embodiments. The following detailed description is, therefore, not to be taken in a limiting sense, and the scope of the present disclosure is defined by the appended claims and their equivalents.

As used herein, an element or step recited in the singular and preceded with the word "a" or "an" should be understood as not excluding plural of said elements or steps, unless such exclusion is explicitly stated. Furthermore, references to "an exemplary embodiment," "various embodiments," "certain embodiments," "a representative embodiment," and the like are not intended to be interpreted as excluding the existence of additional embodiments that also incorporate the recited features. Moreover, unless explicitly stated to the contrary, embodiments "comprising", "including", or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode (2D mode), M-mode, three-dimensional (3D) mode, CF-mode, PW Doppler, CW Doppler, Contrast Enhanced Ultrasound (CEUS), and/or sub-modes of B-mode and/or CF such as Harmonic Imaging, Shear Wave Elasticity Imaging (SWEI), Strain Elastography, TVI, PDI, B-flow, MVI, UGAP, and in some cases also MM, CM, TVD where the "image" and/or "plane" includes a single beam or multiple beams.

Furthermore, the term processor or processing unit, as used herein, refers to any type of processing unit that can carry out the required calculations needed for the various embodiments, such as single or multi-core: CPU, Accelerated Processing Unit (APU), Graphic Processing Unit (GPU), DSP, FPGA, ASIC or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". Also, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIG. 1.

FIG. 1 is a block diagram of an exemplary ultrasound system 100 that is operable to automatically segment and detect a menstrual cycle phase in ultrasound images of anatomical structures that change over a patient menstrual cycle, in accordance with various embodiments. Referring to FIG. 1, there is shown an ultrasound system 100 and a training system 200. The ultrasound system 100 comprises a transmitter 102, an ultrasound probe 104, a transmit beamformer 110, a receiver 118, a receive beamformer 120, A/D converters 122, a RF processor 124, a RF/IQ buffer 126, a user input device 130, a signal processor 132, an image buffer 136, a display system 134, and an archive 138.

The transmitter 102 may comprise suitable logic, circuitry, interfaces and/or code that may be operable to drive an ultrasound probe 104. The ultrasound probe 104 may comprise a two-dimensional (2D) array of piezoelectric elements. The ultrasound probe 104 may comprise a group of transmit transducer elements 106 and a group of receive transducer elements 108, that normally constitute the same elements. In certain embodiment, the ultrasound probe 104 may be operable to acquire ultrasound image data covering at least a substantial portion of an anatomy, such as a uterus, a fetus, a heart, a blood vessel, or any suitable anatomical structure.

The transmit beamformer 110 may comprise suitable logic, circuitry, interfaces and/or code that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 108.

The group of receive transducer elements 108 in the ultrasound probe 104 may be operable to convert the received echoes into analog signals, undergo sub-aperture beamforming by a receive sub-aperture beamformer 116 and are then communicated to a receiver 118. The receiver 118 may comprise suitable logic, circuitry, interfaces and/or code that may be operable to receive the signals from the receive sub-aperture beamformer 116. The analog signals may be communicated to one or a plurality of A/D converters 122.

The plurality of A/D converters 122 may comprise suitable logic, circuitry, interfaces and/or code that may be operable to convert the analog signals from the receiver 118 to corresponding digital signals. The plurality of A/D converters 122 are disposed between the receiver 118 and the RF processor 124. Notwithstanding, the disclosure is not limited in this regard. Accordingly, in some embodiments, the plurality of A/D converters 122 may be integrated within the receiver 118.

The RF processor 124 may comprise suitable logic, circuitry, interfaces and/or code that may be operable to demodulate the digital signals output by the plurality of A/D converters 122. In accordance with an embodiment, the RF processor 124 may comprise a complex demodulator (not shown) that is operable to demodulate the digital signals to form I/Q data pairs that are representative of the corresponding echo signals. The RF or I/Q signal data may then be communicated to an RF/IQ buffer 126. The RF/IQ buffer 126 may comprise suitable logic, circuitry, interfaces and/or code that may be operable to provide temporary storage of the RF or I/Q signal data, which is generated by the RF processor 124.

The receive beamformer 120 may comprise suitable logic, circuitry, interfaces and/or code that may be operable to perform digital beamforming processing to, for example, sum the delayed channel signals received from RF processor 124 via the RF/IQ buffer 126 and output a beam summed signal. The resulting processed information may be the beam summed signal that is output from the receive beamformer 120 and communicated to the signal processor 132. In accordance with some embodiments, the receiver 118, the plurality of A/D converters 122, the RF processor 124, and the beamformer 120 may be integrated into a single beamformer, which may be digital. In various embodiments, the ultrasound system 100 comprises a plurality of receive beamformers 120.

The user input device 130 may be utilized to input patient data, image acquisition and scan parameters, settings, configuration parameters, select protocols and/or templates, change scan mode, and the like. In an exemplary embodiment, the user input device 130 may be operable to configure, manage and/or control operation of one or more components and/or modules in the ultrasound system 100. In this regard, the user input device 130 may be operable to configure, manage and/or control operation of the transmitter 102, the ultrasound probe 104, the transmit beamformer 110, the receiver 118, the receive beamformer 120, the RF processor 124, the RF/IQ buffer 126, the user input device 130, the signal processor 132, the image buffer 136, the display system 134, and/or the archive 138. The user input device 130 may include button(s), rotary encoder(s), a touchscreen, motion tracking, voice recognition, a mousing device, keyboard, camera and/or any other device capable of receiving a user directive. In certain embodiments, one or more of the user input devices 130 may be integrated into other components, such as the display system 134 or the ultrasound probe 104, for example. As an example, user input device 130 may include a touchscreen display.

The signal processor 132 may comprise suitable logic, circuitry, interfaces and/or code that may be operable to process ultrasound scan data (i.e., summed IQ signal) for generating ultrasound images for presentation on a display system 134. The signal processor 132 is operable to perform one or more processing operations according to a plurality of selectable ultrasound modalities on the acquired ultrasound scan data. In an exemplary embodiment, the signal processor 132 may be operable to perform display processing and/or control processing, among other things. Acquired ultrasound scan data may be processed in real-time during a scanning session as the echo signals are received. Additionally or alternatively, the ultrasound scan data may be stored temporarily in the RF/IQ buffer 126 during a scanning session and processed in less than real-time in a live or off-line operation. In various embodiments, the processed image data can be presented at the display system 134 and/or may be stored at the archive 138. The archive 138 may be a local archive, a Picture Archiving and Communication System (PACS), or any suitable device for storing images and related information.

The signal processor 132 may be one or more central processing units, graphic processing units, microprocessors, microcontrollers, and/or the like. The signal processor 132 may be an integrated component, or may be distributed across various locations, for example. In an exemplary embodiment, the signal processor 132 may comprise a segmentation and phase prediction processor 140, a rendering processor 150, and a measurement processor 160 and may be capable of receiving input information from a user input device 130 and/or archive 138, generating an output displayable by a display system 134, and manipulating the output in response to input information from a user input device 130, among other things. The signal processor 132, segmentation and phase prediction processor 140, rendering processor 150, and measurement processor 160 may be capable of executing any of the method(s) and/or set(s) of instructions discussed herein in accordance with the various embodiments, for example.

The ultrasound system 100 may be operable to continuously acquire ultrasound scan data at a frame rate that is suitable for the imaging situation in question. Typical frame rates range from 20-120 but may be lower or higher. The acquired ultrasound scan data may be displayed on the display system 134 at a display-rate that can be the same as the frame rate, or slower or faster. An image buffer 136 is included for storing processed frames of acquired ultrasound scan data that are not scheduled to be displayed immediately. Preferably, the image buffer 136 is of sufficient capacity to store at least several minutes' worth of frames of ultrasound scan data. The frames of ultrasound scan data are stored in a manner to facilitate retrieval thereof according to its order or time of acquisition. The image buffer 136 may be embodied as any known data storage medium.

The signal processor 132 may include a segmentation and phase prediction processor 140 that comprises suitable logic, circuitry, interfaces and/or code that may be operable to receive a two-dimensional (2D) ultrasound image and/or a three-dimensional (3D) ultrasound volume image. The segmentation and phase prediction processor 140 may be configured to automatically segment an anatomical structure from the ultrasound image (e.g., 2D and/or 3D) and predict a menstrual cycle phase. For example, the anatomical structure may have a high variability in shape, appearance, size, and/or echogenicity over a time period. As an example, the anatomical structure may be an endometrium, an ovary, endometrial polyps, fibroids in a uterus, and/or any suitable anatomical structure that changes over a time period. The time period may be a patient menstrual cycle. The menstrual cycle phase may be an identification of the day number of the menstrual cycle, a range of days (e.g., proliferative phase, secretory phase, menstrual phase), or any suitable menstrual cycle phase identification. In various embodiments, the menstrual cycle phase prediction may include a pathological condition prediction, such as endometriosis, endometrial cancer, endometrial polyps, fibroids, endometrial morphology, and the like. The ultrasound image may be a gynecological uterine ultrasound scan, among other things.

The segmentation and phase prediction processor 140 may include image analysis algorithms, artificial intelligence algorithms, one or more deep neural networks (e.g., a convolutional neural network) and/or may utilize any suitable form of image analysis techniques or machine learning processing functionality configured to automatically segment an anatomical structure from the ultrasound image (e.g., 2D and/or 3D) and predict a menstrual cycle phase. The segmentation and phase prediction processor 140 may provide the segmented anatomical structure and predicted menstrual cycle phase to the rendering processor 150 for presentation at the display system 134, provide the segmented anatomical structure and predicted menstrual cycle phase to the measurement processor 160 for performing measurements, and/or store the segmented anatomical structure and predicted menstrual cycle phase at archive 138 and/or any suitable data storage medium.

In various embodiments, the segmentation and phase prediction processor 140 may be provided as a deep neural network that may be made up of, for example, an input layer, an output layer, and one or more hidden layers in between the input and output layers. Each of the layers may be made up of a plurality of processing nodes that may be referred to as neurons. For example, the segmentation and phase prediction processor 140 may include an input layer having a neuron for each pixel or a group of pixels from an ultrasound image, such as a gynecological uterine ultrasound scan. The output layer may have neurons corresponding to a segmented anatomical structure and a predicted menstrual cycle phase. Each neuron of each layer may perform a processing function and pass the processed ultrasound image information to one of a plurality of neurons of a downstream layer for further processing. As an example, neurons of a first layer may learn to recognize edges of structure in the ultrasound image data. The neurons of a second layer may learn to recognize shapes based on the detected edges from the first layer. The neurons of a third layer may learn positions of the recognized shapes relative to landmarks in the ultrasound image data. The processing performed by the segmentation and phase prediction processor 140 deep neural network (e.g., convolutional neural network) may segment anatomical structures and predict a menstrual cycle phase depicted in an ultrasound image with a high degree of probability.

The signal processor 132 may include a rendering processor 150 that comprises suitable logic, circuitry, interfaces and/or code that may be operable to receive from the segmentation and phase prediction processor 140, or retrieve from archive 138 and/or any suitable data storage medium, the segmented anatomical structure and predicted menstrual cycle phase. The rendering processor 150 may be configured to generate one or more renderings of the anatomical structure based on the segmented anatomical structure. For example, the rendering processor 150 may comprise suitable logic, circuitry, interfaces and/or code that may be operable to generate volume renderings, cross-sectional images, an A plane (i.e., the plane parallel to the acquisition plane), a B plane (i.e., the plane perpendicular to the A plane but still parallel to the ultrasound beam), a C plane (i.e., often referred to as the coronal plane, or the two-dimensional slices at various depths from and parallel to the transducer face, and perpendicular to the ultrasound beam), curved slices (i.e., a 2D image slice extracted from a 3D volume along a curved anatomical structure, such as an endometrium of a uterus), and/or any suitable ultrasound images. The rendering processor 150 may be configured to cause a display system 134 to present the generated image(s) with the predicted menstrual cycle phase and/or store the generated image(s) with the predicted menstrual cycle phase at archive 138 and/or any suitable data storage medium.

The signal processor 132 may include a measurement processor 160 that comprises suitable logic, circuitry, interfaces and/or code that may be operable to perform measurements on the segmented anatomical structure. For example, the measurement processor 160 may be configured to perform volume measurements, length measurements, width measurements, and/or any suitable measurements on the segmented anatomical structure. The measurement processor 160 may be configured to cause the display system 134 to present the measurement(s). The measurement processor 160 may be configured to store the measurement(s) at archive 138 and/or any suitable data storage medium.

Still referring to FIG. 1, the display system 134 may be any device capable of communicating visual information to a user. For example, a display system 134 may include a liquid crystal display, a light emitting diode display, and/or any suitable display or displays. The display system 134 can be operable to present the rendering(s) of the segmented anatomical structure, the predicted menstrual cycle phase, measurements, and/or any suitable information.

The archive 138 may be one or more computer-readable memories integrated with the ultrasound system 100 and/or communicatively coupled (e.g., over a network) to the ultrasound system 100, such as a Picture Archiving and Communication System (PACS), a server, a hard disk, floppy disk, CD, CD-ROM, DVD, compact storage, flash memory, random access memory, read-only memory, electrically erasable and programmable read-only memory and/or any suitable memory. The archive 138 may include databases, libraries, sets of information, or other storage accessed by and/or incorporated with the signal processor 132, for example. The archive 138 may be able to store data temporarily or permanently, for example. The archive 138 may be capable of storing medical image data, data generated by the signal processor 132, and/or instructions readable by the signal processor 132, among other things. In various embodiments, the archive 138 stores ultrasound images, segmented anatomical structures, menstrual cycle phase predictions, renderings of the segmented anatomical structures; measurements of the segmented anatomical structures, instructions for segmenting anatomical structures and predicting a menstrual cycle phase, instructions for generating renderings of the segmented anatomical structures, instructions for performing measurements on the segmented anatomical structures, and/or any suitable images, information, and/or instructions, for example.

Components of the ultrasound system 100 may be implemented in software, hardware, firmware, and/or the like. The various components of the ultrasound system 100 may be communicatively linked. Components of the ultrasound system 100 may be implemented separately and/or integrated in various forms. For example, the display system 134 and the user input device 130 may be integrated as a touchscreen display.

Still referring to FIG. 1, the training system 200 may comprise a training engine 210 and a training database 220. The training engine 210 may comprise suitable logic, circuitry, interfaces and/or code that may be operable to train the neurons of the deep neural network (e.g., artificial intelligence classification adapted segmentation network) inferenced (i.e., deployed) by the segmentation and phase prediction processor 140. For example, the classification adapted segmentation network inferenced by the segmentation and phase prediction processor 140 may be trained to automatically segment an anatomical structure depicted in an ultrasound image and predict a menstrual cycle phase. As an example, the training engine 210 may train the classification adapted segmentation network deployed by the segmentation and phase prediction processor 140 to automatically segment an anatomical structure depicted in an ultrasound image and predict a menstrual cycle phase using database(s) 220 of classified anatomical structures and corresponding phase labels. The classified anatomical structures may include an input image and a ground truth binary image (i.e., mask) of the manually segmented anatomical structure. The training engine 210 may be configured to optimize the classification adapted segmentation network by adjusting the weighting of the classification adapted segmentation network to minimize a segmentation loss function between the input ground truth mask and an output predicted mask. The phase labels may be the day number of the menstrual cycle, a range of days (e.g., proliferative phase, secretory phase, menstrual phase), or any suitable menstrual cycle phase identification. The training engine 210 may be configured to optimize the classification adapted segmentation network by adjusting the weighting of the classification adapted segmentation network to minimize a classification loss function between the input phase label and an output predicted phase.

In various embodiments, the databases 220 of training images may be a Picture Archiving and Communication System (PACS), or any suitable data storage medium. In certain embodiments, the training engine 210 and/or training image databases 220 may be remote system(s) communicatively coupled via a wired or wireless connection to the ultrasound system 100 as shown in FIG. 1. Additionally and/or alternatively, components or all of the training system 200 may be integrated with the ultrasound system 100 in various forms.

Figure 2:
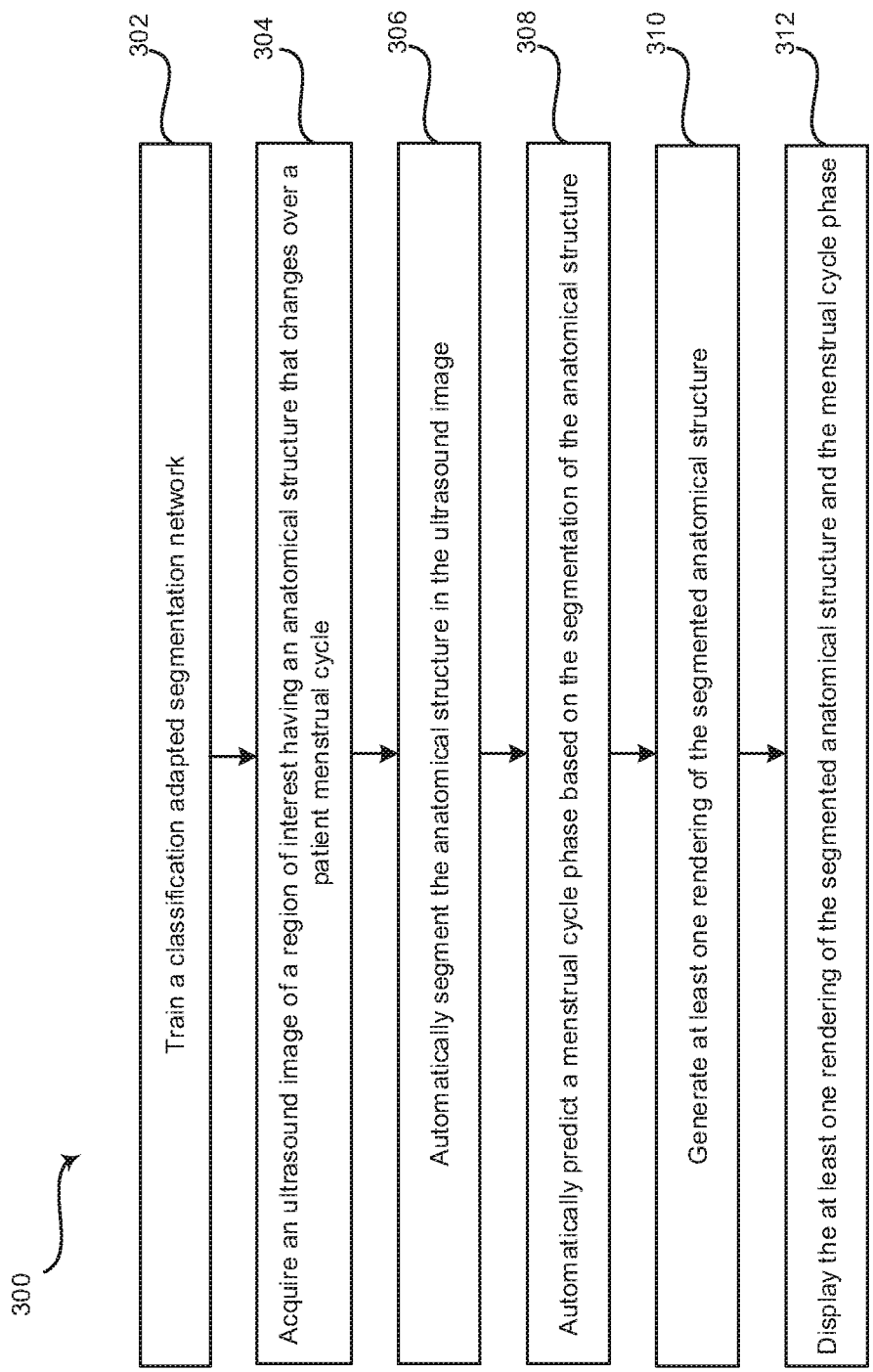
FIG. 2 is a flow chart illustrating exemplary steps that may be utilized for automatically segmenting and detecting a menstrual cycle phase in ultrasound images of anatomical structures that change over a patient menstrual cycle, in accordance with various embodiments.

FIG. 2 is a flow chart 300 illustrating exemplary steps 302-312 that may be utilized for automatically segmenting and detecting a menstrual cycle phase in ultrasound images of anatomical structures that change over a patient menstrual cycle, in accordance with various embodiments. Referring to FIG. 2, there is shown a flow chart 300 comprising exemplary steps 302 through 312. Certain embodiments may omit one or more of the steps, and/or perform the steps in a different order than the order listed, and/or combine certain of the steps discussed below. For example, some steps may not be performed in certain embodiments. As a further example, certain steps may be performed in a different temporal order, including simultaneously, than listed below.

At step 302, a classification adapted segmentation network is trained for automatically segmenting anatomical structures that change over a time period, and for predicting a phase of the time period. For example, a training engine 210 of a training system 200 trains the classification adapted segmentation network using database(s) 220 of classified anatomical structures and corresponding phase labels. The classified anatomical structures may include an input image and a ground truth binary image (i.e., mask) of the manually segmented anatomical structure. The training engine 210 may be configured to optimize the classification adapted segmentation network by adjusting the weighting of the classification adapted segmentation network to minimize a segmentation loss function between the input ground truth mask and an output predicted mask. The phase labels may be the day number of the menstrual cycle, a range of days (e.g., proliferative phase, secretory phase, menstrual phase), or any suitable menstrual cycle phase identification. In various embodiments, the phase labels may include a pathological condition label, such as endometriosis, endometrial cancer, endometrial polyps, fibroids, endometrial morphology, and the like. The training engine 210 may be configured to optimize the classification adapted segmentation network by adjusting the weighting of the classification adapted segmentation network to minimize a classification loss function between the input phase label and an output predicted phase. The classification adapted segmentation network may be a single network operable to both automatically segment the anatomical structure from a 2D or 3D ultrasound image, and predict a menstrual cycle phase. For example, the anatomical structure may have a high variability in shape, appearance, size, and/or echogenicity over a time period. As an example, the anatomical structure may be an endometrium, an ovary, endometrial polyps, fibroids in a uterus, and/or any suitable anatomical structure that changes over a time period. The time period may be a patient menstrual cycle. The input image may be a gynecological uterine ultrasound scan, among other things.

At step 304, an ultrasound probe 104 of an ultrasound system 100 acquires an ultrasound image of a region of interest having an anatomical structure that changes over a patient menstrual cycle. For example, the ultrasound probe 104 may be navigated to perform a gynecological uterine ultrasound scan, among other things. The acquired ultrasound image may be presented at a display system 134 of the ultrasound system 100, provided to a segmentation and phase prediction processor 140 of the signal processor 132 of the ultrasound system 100, and/or stored at archive 138 of the ultrasound system 100 and/or any suitable data storage medium.

At step 306, a signal processor 132 of the ultrasound system 100 may automatically segment the anatomical structure in the ultrasound image. For example, a segmentation and phase prediction processor 140 of the signal processor 132 may be configured to deploy the classification adapted segmentation network trained at step 302 to automatically segment the anatomical structure in the ultrasound image received from the ultrasound probe 104 or retrieved from the archive 138 and/or any suitable data storage medium.

At step 308, the signal processor 132 of the ultrasound system 100 may automatically predict a menstrual cycle phase based on the segmentation of the anatomical structure. For example, the segmentation and phase prediction processor 140 of the signal processor 132 may be configured to simultaneously inference the classification adapted segmentation network deployed at step 306 to predict the menstrual cycle phase while segmenting the anatomical structure. The menstrual cycle phase prediction may be based on an appearance of the segmented anatomical structure. The menstrual cycle phase may be the day number of the menstrual cycle, a range of days (e.g., proliferative phase, secretory phase, menstrual phase), or any suitable menstrual cycle phase identification. The segmentation and phase prediction processor 140 may provide the segmented anatomical structure from step 306 and the predicted menstrual cycle phase to the rendering processor 150 for presentation at the display system 134, provide the segmented anatomical structure and predicted menstrual cycle phase to the measurement processor 160 for performing measurements, and/or store the segmented anatomical structure and predicted menstrual cycle phase at archive 138 and/or any suitable data storage medium.

At step 310, the signal processor 132 of the ultrasound system 100 may generate at least one rendering of the segmented anatomical structure. For example, a rendering processor 150 of the signal processor 132 may be configured to receive the segmented anatomical structure from step 306 and the predicted menstrual cycle phase from step 308 from the segmentation and phase prediction processor 140 and/or may retrieve the segmented anatomical structure and the predicted menstrual cycle phase from archive 138 and/or any suitable data storage medium. The rendering processor 150 may be configured to generate one or more renderings of the anatomical structure based on the segmented anatomical structure. For example, the rendering processor 150 may comprise suitable logic, circuitry, interfaces and/or code that may be operable to generate volume renderings, cross-sectional images, an A plane, a B plane, a C plane, curved slices, and/or any suitable ultrasound images. In various embodiments, a measurement processor 160 may be configured to receive the segmented anatomical structure from step 306 and the predicted menstrual cycle phase from step 308 from the segmentation and phase prediction processor 140 and/or may retrieve the segmented anatomical structure and the predicted menstrual cycle phase from archive 138 and/or any suitable data storage medium. The measurement processor 160 may be configured to perform volume measurements, length measurements, width measurements, and/or any suitable measurements on the segmented anatomical structure. The measurement processor 160 may be configured to provide the measurement(s) to the rendering processor 150, display the measurement(s) at display system 134, and/or store the measurement(s) at archive 138 and/or any suitable data storage medium.

At step 312, the signal processor 132 may cause a display system of the ultrasound system 100 to present the at least one rendering of the segmented anatomical structure and the menstrual cycle phase. For example, the rendering processor 150 may be configured to cause a display system 134 to present the image(s) generated at step 310 with the predicted menstrual cycle phase. Additionally and/or alternatively, the rendering processor 150 may be configured to store the generated image(s) with the predicted menstrual cycle phase at archive 138 and/or any suitable data storage medium. In various embodiments, the rendering processor 150 and/or measurement processor 160 may be configured to cause the display system 134 to further present any measurement(s) performed by the measurement processor 160 at step 310.

Aspects of the present disclosure provide a method 300 and system 100 for automatically segmenting and detecting a menstrual cycle phase in ultrasound images of anatomical structures that change over a patient menstrual cycle. In accordance with various embodiments, the method 300 may comprise acquiring 304, by an ultrasound probe 104 of an ultrasound system 100, an ultrasound image of a region of interest having an anatomical structure that changes over a patient menstrual cycle. The method 300 may comprise automatically segmenting 306, by at least one processor 132, 140 of the ultrasound system 100, the anatomical structure depicted in the ultrasound image. The method 300 may comprise automatically predicting 308, by the at least one processor 132, 140, a menstrual cycle phase based on the segmentation of the anatomical structure. The method 300 may comprise causing 312, by the at least one processor 132, 150, a display system 134 to present at least one rendering of the segmented anatomical structure and the predicted menstrual cycle phase.

In a representative embodiment, the method 300 may comprise generating 310, by the at least one processor 132, 150, the at least one rendering of the segmented anatomical structure. The at least one rendering may comprise a volume rendering, a cross-sectional image, an A plane, a B plane, a C plane, and/or a curved slice. In an exemplary embodiment, the automatically segmenting the anatomical structure and the automatically predicting the menstrual cycle phase is performed by inferencing a single classification adapted segmentation network. The menstrual cycle phase may be one of a day number of the patient menstrual cycle, or a range of days of the patient menstrual cycle. In certain embodiments, the method 300 may comprise training 302 the single classification adapted segmentation network. The training 302 may comprise receiving, by a training engine 210 of a training system 200, an input image, a ground truth mask, and phase label. The training 302 may comprise adjusting, by the training engine 210, a weighting of the single classification adapted segmentation network to reduce a segmentation loss function between the ground truth mask and an output predicted mask. The training 302 may comprise adjusting, by the training engine 210, the weighting of the single classification adapted segmentation network to reduce a classification loss function between the phase label and an output predicted phase. The phase label may be one of a day number of the patient menstrual cycle, or a range of days of the patient menstrual cycle. In various embodiments, the ultrasound image is a gynecological uterine ultrasound image, and one of a two-dimensional (2D) ultrasound image or a three-dimensional (3D) ultrasound image. In a representative embodiment, the phase label comprises a pathological condition label comprising at least one of endometriosis, endometrial cancer, endometrial polyp, fibroid, or endometrial morphology. In an exemplary embodiment, the method 300 may comprise performing 310, by the at least one processor 132, 160, a volume measurement of the segmented anatomical structure. The method 300 may comprise causing 312, by the at least one processor 132, 150, 160, the display system 134 to present the volume measurement. In certain embodiments, the anatomical structure is one of an endometrium, an ovary, endometrial polyps, or fibroids in a uterus.

Various embodiments provide a system 100 for automatically segmenting and detecting a menstrual cycle phase in ultrasound images of anatomical structures that change over a patient menstrual cycle. The system 100 may comprise an ultrasound probe 104, at least one processor 132, 140, 150, 160, and a display system 134. The ultrasound probe 104 may be operable to acquire an ultrasound image of a region of interest having an anatomical structure that changes over a patient menstrual cycle. The at least one processor 132, 140 may be configured to automatically segment the anatomical structure depicted in the ultrasound image. The at least one processor 132, 140 may be configured to automatically predict a menstrual cycle phase based on the segmentation of the anatomical structure. The display system 134 may be configured to present at least one rendering of the segmented anatomical structure and the predicted menstrual cycle phase.

In an exemplary embodiment, the at least one processor 132, 150 is configured to render the segmented anatomical structure to generate the at least one rendering. The at least one rendering may comprise a volume rendering, a cross-sectional image, an A plane, a B plane, a C plane, and/or a curved slice. In certain embodiments, the at least one processor 132, 140 is configured to inference a single classification adapted segmentation network to automatically segment the anatomical structure and automatically predict the menstrual cycle phase. The menstrual cycle phase may be one of a day number of the patient menstrual cycle, or a range of days of the patient menstrual cycle. In various embodiments, the ultrasound system 100 is communicatively coupled to or comprises a training system 200 configured to train the single classification adapted segmentation network. The training system 200 may comprise a training engine 210 configured to receive an input image, a ground truth mask, and a phase label. The training engine 210 may be configured to adjust a weighting of the single classification adapted segmentation network to reduce a segmentation loss function between the ground truth mask and an output predicted mask. The training engine 210 may be configured to adjust the weighting of the single classification adapted segmentation network to reduce a classification loss function between the phase label and an output predicted phase. The phase label may be one of a day number of the patient menstrual cycle, or a range of days of the patient menstrual cycle. In a representative embodiment, the phase label comprises a pathological condition label comprising at least one of endometriosis, endometrial cancer, endometrial polyp, fibroid, or endometrial morphology. In an exemplary embodiment, the at least one processor 132, 160 is configured to perform a volume measurement of the segmented anatomical structure. The at least one processor 132, 150, 160 may be configured to cause the display system 134 to present the volume measurement. In various embodiments, the anatomical structure is one of an endometrium, an ovary, endometrial polyps, or fibroids in a uterus.

Certain embodiments provide a non-transitory computer readable medium having stored thereon, a computer program having at least one code section. The at least one code section is executable by a machine for causing an ultrasound system 100 to perform steps 300. The steps 300 may comprise receiving 304, from an ultrasound probe 104 of the ultrasound system 100, an ultrasound image of a region of interest having an anatomical structure that changes over a patient menstrual cycle. The steps 300 may comprise automatically segmenting 306 the anatomical structure depicted in the ultrasound image. The steps 300 may comprise automatically predicting 308 a menstrual cycle phase based on the segmentation of the anatomical structure. The steps 300 may comprise causing 312 a display system 134 to present at least one rendering of the segmented anatomical structure and the predicted menstrual cycle phase.

In various embodiments, the anatomical structure is one of an endometrium, an ovary, endometrial polyps, or fibroids in a uterus. In a representative embodiment, the automatically segmenting the anatomical structure and the automatically predicting the menstrual cycle phase is performed by inferencing a single classification adapted segmentation network. The menstrual cycle phase may be one of a day number of the patient menstrual cycle, or a range of days of the patient menstrual cycle. In an exemplary embodiment, the steps 300 may comprise training 302 the single classification adapted segmentation network. The training 302 may comprise receiving an input image, a ground truth mask, and a phase label. The training 302 may comprise adjusting a weighting of the single classification adapted segmentation network to reduce a segmentation loss function between the ground truth mask and an output predicted mask. The training 302 may comprise adjusting the weighting of the single classification adapted segmentation network to reduce a classification loss function between the phase label and an output predicted phase. The phase label may be one of a day number of the patient menstrual cycle, or a range of days of the patient menstrual cycle. In certain embodiments, the phase label comprises a pathological condition label comprising at least one of endometriosis, endometrial cancer, endometrial polyp, fibroid, or endometrial morphology.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set {(x), (y), (x, y)}. As another example, "x, y, and/or z" means any element of the seven-element set {(x), (y), (z), (x, y), (x, z), (y, z), (x, y, z)}. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" and/or "configured" to perform a function whenever the circuitry comprises the necessary hardware and code (if any is necessary) to perform the function, regardless of whether performance of the function is disabled, or not enabled, by some user-configurable setting.

Other embodiments may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for automatically segmenting and detecting a menstrual cycle phase in ultrasound images of anatomical structures that change over a patient menstrual cycle.

Accordingly, the present disclosure may be realized in hardware, software, or a combination of hardware and software. The present disclosure may be realized in a centralized fashion in at least one computer system, or in a distributed fashion where different elements are spread across several interconnected computer systems. Any kind of computer system or other apparatus adapted for carrying out the methods described herein is suited.

Various embodiments may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What is claimed is:

1. A method comprising:
    acquiring, by an ultrasound probe of an ultrasound system, an ultrasound image of a region of interest having an anatomical structure that changes over a patient menstrual cycle;
    automatically segmenting, by at least one processor of the ultrasound system, the anatomical structure depicted in the ultrasound image;
    automatically predicting, by the at least one processor, a menstrual cycle phase based on the segmentation of the anatomical structure; and
    causing, by the at least one processor, a display system to present at least one rendering of the segmented anatomical structure and the predicted menstrual cycle phase.

2. The method of claim 1, comprising generating, by the at least one processor, the at least one rendering of the segmented anatomical structure, wherein the at least one rendering comprises:
    a volume rendering,
    a cross-sectional image,
    an A plane,
    a B plane,
    a C plane, and/or
    a curved slice.

3. The method of claim 1, wherein:
    the automatically segmenting the anatomical structure and the automatically predicting the menstrual cycle phase is performed by inferencing a single classification adapted segmentation network; and
    the menstrual cycle phase is one of:
        a day number of the patient menstrual cycle, or
        a range of days of the patient menstrual cycle.

4. The method of claim 3, comprising training the single classification adapted segmentation network, the training comprising:
    receiving, by a training engine of a training system, an input image, a ground truth mask, and a phase label;
    adjusting, by the training engine, a weighting of the single classification adapted segmentation network to reduce a segmentation loss function between the ground truth mask and an output predicted mask; and
    adjusting, by the training engine, the weighting of the single classification adapted segmentation network to reduce a classification loss function between the phase label and an output predicted phase,
    wherein the phase label is one of:
        a day number of the patient menstrual cycle, or
        a range of days of the patient menstrual cycle.

5. The method of claim 1, wherein the ultrasound image is:
a gynecological uterine ultrasound image; and
one of a two-dimensional (2D) ultrasound image or a three-dimensional (3D) ultrasound image.

6. The method of claim 3, wherein the phase label comprises a pathological condition label comprising at least one of:
endometriosis,
endometrial cancer,
endometrial polyp,
fibroid, or
endometrial morphology.

7. The method of claim 1, comprising:
performing, by the at least one processor, a volume measurement of the segmented anatomical structure; and
causing, by the at least one processor, the display system to present the volume measurement.

8. The method of claim 1, wherein the anatomical structure is one of:
an endometrium,
an ovary,
endometrial polyps, or
fibroids in a uterus.

9. An ultrasound system comprising:
an ultrasound probe operable to acquire an ultrasound image of a region of interest having an anatomical structure that changes over a patient menstrual cycle;
at least one processor configured to:
automatically segment the anatomical structure depicted in the ultrasound image; and
automatically predict a menstrual cycle phase based on the segmentation of the anatomical structure; and
a display system configured to present at least one rendering of the segmented anatomical structure and the predicted menstrual cycle phase.

10. The ultrasound system of claim 9, wherein the at least one processor is configured to render the segmented anatomical structure to generate the at least one rendering, wherein the at least one rendering comprises:
a volume rendering,
a cross-sectional image,
an A plane,
a B plane,
a C plane, and/or
a curved slice.

11. The ultrasound system of claim 9, wherein:
the at least one processor is configured to inference a single classification adapted segmentation network to automatically segment the anatomical structure and automatically predict the menstrual cycle phase; and
the menstrual cycle phase is one of:
a day number of the patient menstrual cycle, or
a range of days of the patient menstrual cycle.

12. The ultrasound system of claim 11, wherein the ultrasound system is communicatively coupled to or comprises a training system configured to train the single classification adapted segmentation network, the training system comprising a training engine configured to:
receive an input image, a ground truth mask, and a phase label;
adjust a weighting of the single classification adapted segmentation network to reduce a segmentation loss function between the ground truth mask and an output predicted mask; and
adjust the weighting of the single classification adapted segmentation network to reduce a classification loss function between the phase label and an output predicted phase,
wherein the phase label is one of:
a day number of the patient menstrual cycle, or
a range of days of the patient menstrual cycle.

13. The ultrasound system of claim 12, wherein the phase label comprises a pathological condition label comprising at least one of:
endometriosis,
endometrial cancer,
endometrial polyp,
fibroid, or
endometrial morphology.

14. The ultrasound system of claim 9, wherein the at least one processor is configured to:
perform a volume measurement of the segmented anatomical structure; and
cause the display system to present the volume measurement.

15. The ultrasound system of claim 9, wherein the anatomical structure is one of:
an endometrium,
an ovary,
endometrial polyps, or
fibroids in a uterus.

16. A non-transitory computer readable medium having stored thereon, a computer program having at least one code section, the at least one code section being executable by a machine for causing an ultrasound system to perform steps comprising:
receiving, from an ultrasound probe of the ultrasound system, an ultrasound image of a region of interest having an anatomical structure that changes over a patient menstrual cycle;
automatically segmenting the anatomical structure depicted in the ultrasound image;
automatically predicting a menstrual cycle phase based on the segmentation of the anatomical structure; and
causing a display system to present at least one rendering of the segmented anatomical structure and the predicted menstrual cycle phase.

17. The non-transitory computer readable medium of claim 16, wherein the anatomical structure is one of:
an endometrium,
an ovary,
endometrial polyps, or
fibroids in a uterus.

18. The non-transitory computer readable medium of claim 16, wherein:
the automatically segmenting the anatomical structure and the automatically predicting the menstrual cycle phase is performed by inferencing a single classification adapted segmentation network; and
the menstrual cycle phase is one of:
a day number of the patient menstrual cycle, or
a range of days of the patient menstrual cycle.

19. The non-transitory computer readable medium of claim 18, comprising training the single classification adapted segmentation network, the training comprising:
receiving an input image, a ground truth mask, and a phase label;
adjusting a weighting of the single classification adapted segmentation network to reduce a segmentation loss function between the ground truth mask and an output predicted mask; and adjusting the weighting of the single classification adapted segmentation network to reduce a classification loss function between the phase label and an output predicted phase, wherein the phase label is one of:
  a day number of the patient menstrual cycle, or
  a range of days of the patient menstrual cycle.

20. The non-transitory computer readable medium of claim 19, wherein the phase label comprises a pathological condition label comprising at least one of:
  endometriosis,
  endometrial cancer,
  endometrial polyp,
  fibroid, or
  endometrial morphology.

* * * * *